United States Patent [19]

Reddy et al.

[11] Patent Number: 5,518,651
[45] Date of Patent: May 21, 1996

[54] METHODS AND REAGENTS FOR CLEAVING AND DEPROTECTING OLIGONUCLEOTIDES

[75] Inventors: Parameswara M. Reddy, Brea; Naeem B. Hanna, Fullerton, both of Calif.

[73] Assignee: Beckman Instruments, Inc., Fullerton, Calif.

[21] Appl. No.: 257,964

[22] Filed: Jun. 8, 1994

Related U.S. Application Data

[62] Division of Ser. No. 873,915, Apr. 24, 1992, Pat. No. 5,348,868.

[51] Int. Cl.$^6$ ............. C12P 19/34; C07H 19/10; C07H 19/06; C07H 19/073
[52] U.S. Cl. ............. 252/193; 435/91.1; 536/25.3; 536/25.31; 536/26.8; 536/28.51
[58] Field of Search ............. 435/91.1; 536/25.3, 536/25.31, 26.8, 28.51; 252/193

[56] References Cited

U.S. PATENT DOCUMENTS

| | | | |
|---|---|---|---|
| 4,033,977 | 7/1977 | Philipp et al. | 548/153 |
| 4,242,097 | 12/1980 | Rich et al. | 436/100 |
| 4,415,732 | 11/1983 | Caruthers et al. | 536/27 |
| 4,450,277 | 5/1984 | Graf et al. | 548/335.5 |
| 4,680,295 | 7/1987 | Fowler et al. | 514/258 |
| 5,001,264 | 3/1991 | Saeki et al. | 564/412 |
| 5,296,023 | 3/1994 | Gregory et al. | 540/130 |

FOREIGN PATENT DOCUMENTS

| | | |
|---|---|---|
| 0241363 | 10/1987 | European Pat. Off. . |
| 0323152 | 7/1989 | European Pat. Off. . |

OTHER PUBLICATIONS

Adrich Catalogue 1988–1989 p. 983 "Methylamine 40 wt % Solution in Water" #M2,775–1.

Bhat, V. et al "A Simple and Convenient Method for the Selective N–Acylatrims of Cytosine Nucleotides" Nucleosides & Nucleotides 8(2): 179–183 (1989).

Chaix, C., et al. "The Use of Labile Base Protecting Groups in Oligonucleotide Synthesis" Tetrahedron Letters 30(1): 71–74 (1989).

Singh, R. K., et al. "Protecting Groups Used in Oligonucleotide Synthesis: A Current Survey" J. Sci. & Ind. Res. 49: 441–448 (1990).

Köster, H. "N–Acyl Protecting Groups for Deoxynucleotides: A Quantitative and Comparative Study" Tetrahedron 37: 363–369 (1981).

Chaix, C., et al. "Solid Phase Synthesis of the 5'–Half of the Initiator t–RNA From B. Subtilis" Nuc. Acid Res. 17(18): 7381–7393 (1989).

Weber H. & Khorana, H. G. "CIV. Total Synthesis of the Structured Gene for an Alanine Transfer Ribonucleic Acid From Yeast" J. Vol. Biol. 72: 219–249 (1972).

Vu, H., et al "Fast Oligonucleotide Deprotection Phosphoramidite Chemistry for DNA Synthesis" Tetrahedron Letters 31(50): 7269–7272 (1990).

Sinha, N. D., et al. "Polymer Support Oligonucleotide Synthesis XVIII" Nuc. Acids Res. 12(11): 4539–4556 (1984).

McBride, L. J. & Caruthers, M. H. "An Investigation of Several Oligonucleotide Phosphoramidites Useful for Synthesizing Deoxynucleotides" Tetrahedron Letters 24(3): 245–248 (1983).

Primary Examiner—Herbert J. Lilling
Attorney, Agent, or Firm—William H. May; Janis C. Henry; Arnold Grant

[57] ABSTRACT

Disclosed are reagents of methods for cleaving and deprotecting insolubilized and protected synthetic oligonucleotides. In a particularly preferred embodiment, the reagent comprises methylamine and t-butylamine.

2 Claims, 7 Drawing Sheets

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: No ( i v ) ANTI-SENSE: No ( x i ) SEQUENCE DESCRIPTION: SEQ ID NO:1:

CTG GAC AGT AGT CAG ACT GCT     2 1

( 2 ) INFORMATION FOR SEQ ID NO: 2:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:2:

GTG GAC GCT AGG GCG GAG CCT　　　　　　　　　　　　　　　　　　21

( 2 ) INFORMATION FOR SEQ ID NO: 3:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:3:

GGG GGG GGG GGG GGG GGG GGG　　　　　　　　　　　　　　　　　　21

( 2 ) INFORMATION FOR SEQ ID NO: 4:

( i ) SEQUENCE CHARACTERISTICS:
    ( A ) LENGTH: 35 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:4:

CAG TGC AGC TCC TAG CAG CCT AGC GTA CTA GTC TT　　　　　　　　35

( 2 ) INFORMATION FOR SEQ ID NO: 5:

( i ) SEQUENCE CHARACTERISTICS:
    ( A ) LENGTH: 51 bases
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:5:

CAG TCC TAG TCA CAG TCC AGT CGC TCA AGC GTC CAG　　　　　　　　36

TTG CAC AGG TCA CCT　　　　　　　　　　　　　　　　　　　　　　51

( 2 ) INFORMATION FOR SEQ ID NO: 6:

( i ) SEQUENCE CHARACTERISTICS:
    ( A ) LENGTH: 101 bases (B) TYPE: nucleic acid
(C) STRANDEDNESS: single
(D) TOPOLOGY: linear (ii) MOLECULE TYPE: DNA (genomic)

(iii) HYPOTHETICAL: no (iv) ANTI-SENSE: no (xi) SEQUENCE DESCRIPTION: SEQ ID NO:6:

| | | | | | | | | | | | | |
|---|---|---|---|---|---|---|---|---|---|---|---|---|
| GCT | GCC | AGT | TCG | GTC | ATC | CGA | TCC | TCG | GTC | ACG | CAA | 36 |
| CTG | TCA | ACG | GCA | CCT | ACT | CCT | CGT | AAC | GTA | GGA | CAG | 72 |
| TCC | GAT | TCG | CAC | GTG | CAA | AGC | CCA | TTC | AT | | | 101 |

(2) INFORMATION FOR SEQ ID NO: 7:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: DNA (genomic)

(iii) HYPOTHETICAL: no (iv) ANTI-SENSE: no (xi) SEQUENCE DESCRIPTION: SEQ ID NO:7:

AGC TAC GGT CAT CGT ATG CAT                                          21

(2) INFORMATION FOR SEQ ID NO:8:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:8:

ATG CAT ACG ATG ACC GTA GCT                                          21

(2) INFORMATION FOR SEQ ID NO:9:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:9:

CGC CAG GGT TTT CCC AGT                                              18

(2) INFORMATION FOR SEQ ID NO:10:

(i) SEQUENCE CHARACTERISTICS:
(A) LENGTH: 22 bases (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:10:

TTC TGG CGT ACC GTT CCT GTC T   22

(2) INFORMATION FOR SEQ ID NO:11:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:11:

CGC CAG GGT TTT CCC AGT   18

(2) INFORMATION FOR SEQ ID NO:12:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (genomic)

(iii) HYPOTHETICAL: No (iv) ANTI-SENSE: No (xi) SEQUENCE DESCRIPTION: SEQ ID NO:12:

TTC TGG CGT ACC GTT CCT GTC T   22

METHODS AND REAGENTS FOR CLEAVING AND DEPROTECTING OLIGONUCLEOTIDES

RELATED APPLICATION

The present application is a divisional application of U.S. application Ser. No. 07/873,915, filed Apr. 24, 1992, now U.S. Pat. No. 5,348,868.

The present application is related to U.S. Ser. No.. 07/873,330 (Beckman Docket No. 128D-1007) for "Protecting Groups Useful In Oligonucleotide Synthesis" by Parameswara Meda Reddy and Naeem Botros Hanna, which is filed simultaneously herewith. The related application is incorporated fully herein by reference.

FIELD OF INVENTION

The present invention relates generally to the synthesis of oligonucleotides and more particularly to methods and reagents for cleaving oligonucleotides from solid supports, and removing protecting groups from oligonucleotides.

BACKGROUND OF THE INVENTION

Deoxyribonucleic acid ("DNA") and ribonucleic acid ("RNA") are long, threadlike macromolecules, DNA comprising a chain of deoxyribonucleotides, and RNA comprising a chain of ribonucleotides. A nucleotide consists of a nucleoside and one or more phosphate groups; a nucleoside consists of a nitrogenous base linked to a pentose sugar. Typically, the phosphate group is attached to the fifth-carbon ("C-5") hydroxyl group ("OH") of the pentose sugar; however, it can also be attached to the third-carbon hydroxyl group ("C-3 OH"). In a molecule of DNA, the pentose sugar is deoxyribose, while in a molecule of RNA, the pentose sugar is ribose. The nitrogenous bases in DNA are adenine ("A"), cytosine ("C"), guanine ("G"), and thymine ("T"). These bases are the same for RNA, except that uracil ("U") replaces thymine. Accordingly, the major nucleosides of DNA, collectively referred to as "deoxynucleosides" are as follows: deoxyadenosine ("dA"); deoxycytidine ("dC"); deoxyguanosine ("dG"); and thymidine ("T"). The corresponding ribonucleosides are designated as "A"; "C"; "G"; and "U". (By convention, and because there is no corresponding thymidine ribonucleoside, deoxythymidine is typically designated as "T"; for consistency purposes, however, thymidine will be designated as "dT" throughout this disclosure).

The sequence of the nitrogenous bases of the DNA or RNA molecule encodes the genetic information contained in the molecule. The sugar and phosphate groups of a DNA or RNA molecule perform a structural role, forming the backbone of the molecule. Specifically, the sugar moiety of each nucleotide is linked to the sugar moiety of the adjacent nucleotide such that the 3'-hydroxyl of the pentose sugar of one nucleotide is linked to the 5'-hydroxyl of the pentose sugar of the adjacent nucleotide. The linkage between the two pentose sugars is typically via a phosphodiester bond. Based upon this linkage protocol, one end ("terminus") of the nucleotide chain has a 5'-terminus (e.g. hydroxyl, triphosphate, etc.), and the other end has a 3'-hydroxyl group. By convention, the base sequence of a nucleotide chain is written in a 5' to 3' direction, i.e., 5'-ATCG-3' or simply ATCG DNA and RNA are produced internally by living animals; however, DNA and RNA can be chemically synthesized such that synthetic strands of DNA and RNA can be rapidly and efficiently produced. These strands are typically referred to as "synthetic oligonucleotides" or "oligonucleotides." A widely utilized chemical procedure for the synthesis of oligonucleotides is referred to as the "phosphoramidite methodology." See, e.g., U.S. Pat. No. 4,415,732; McBride, L. and Caruthers, M. *Tetrahedron Letters*, 24:245–248 (1983); and Sinha, N. et al. *Nucleic Acid Res.* 12:4539–4557 (1984), which are all incorporated herein by reference. Commercially available oligonucleotide synthesizers based upon the phosphoramidite methodology include, e.g., the Biosearch 8750™ and ABI 380B™, 392™ and 394™ DNA synthesizers.

The importance of chemically synthesized oligonucleotides is principally due to the wide variety of applications to which oligonucleotides can be directed. For example, oligonucleotides can be utilized in biological studies involving genetic engineering, recombinant DNA techniques, antisense DNA, detection of genomic DNA, probing DNA and RNA from various systems, detection of protein-DNA complexes, detection of site directed mutagenesis, primers for DNA and RNA synthesis, primers for amplification techniques such as the polymerase chain reaction, ligase chain reaction, etc, templates, linkers, and molecular interaction studies.

The primary structures of DNA and RNA molecules can be depicted as follows:

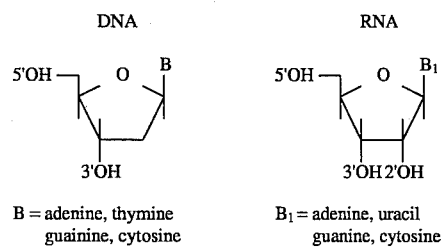

B = adenine, thymine guanine, cytosine $B_1$ = adenine, uracil guanine, cytosine The key step in nucleic acid synthesis is the specific and sequential formation of internucleotide phosphate linkages between a 5'-OH group of one nucleotide and a 3'-OH group of another nucleotide. Accordingly, in the typical synthesis of oligonucleotides, the phosphate group of an "incoming" nucleotide is combined with the 5'-OH group of another nucleotide (i.e. the 5'-OH group is "phosphorylated" or "phosphitylated"). These groups must be capable of actively participating in the synthesis of the oligonucleotides. Thus, the 5'-OH groups are modified (typically with a dimethoxy trityl ("DMT") group) such that an investigator can introduce two such nucleotides into a reaction chamber and adjust the conditions therein so that the two nucleotides are properly combined; by a series of successive such additions, a growing oligonucleotide having a defined sequence can be accurately generated.

The four bases of the nucleosides, adenine, thymine (uracil in the case of RNA), guanine and cytosine, include moieties which are chemically reactive (e.g., exocyclic amino groups). These groups must be "temporarily" protected, i.e. the protecting groups must be capable of blocking any reactive sites on the base until after the oligonucleotide synthesis is completed; after such synthesis is completed, these groups must also be capable of being removed from the bases such that the biological activity of the oligonucleotide is not affected. Without protecting the amino groups of dA, dC, dG (or the corresponding ribonucleotides in the case of RNA synthesis), undesirable and/or less useful material will be synthesized. Thymine (T), which does not have an amino group, does not typically require a protecting group. The traditional amino protecting group for dA is a benzoyl group ("bz"); for dC, a bz group or an isobutyryl group ("ibu"); and for dG, ibu. It is conventional to indicate which protecting group is being utilized as follows: dA$^{bz}$, indicating that a benzoyl protecting group is being used to protect the adenine exocyclic amino group.

In order to maintain an additional degree of control over oligonucleotide synthesis, it is necessary to initiate the synthesis of the oligonucleotides from an insolubilized starting point. I.e., the oligonucleotide is synthesized while "tethered" to an appropriate solid support. This protocol increases the speed and convenience of the synthesis as compared to solution-based oligonucleotide synthesis. Accordingly, the synthesis of oligonucleotides requires, as a final step or steps, the removal of protecting groups from the oligonucleotide ("deprotection") and release ("cleavage") of the oligonucleotide from a solid support material—such steps are required in order to generate a biologically useful oligonucleotide.

"Deprotection" is defined as the process and the time necessary for removal of protecting groups incorporated into the nucleotides; "cleavage" is defined as the process and the time necessary for removal of the synthesized oligonucleotide from a solid support material onto which the nucleotides have been attached.

Deprotection of dG is the rate limiting step for oligonucleotide deprotection. By convention, those in the art will focus on the time necessary to deprotect deoxyguanosine incorporated into the oligonucleotide. With respect to side-product formation (i.e. the formation of undesirable materials), deoxycytidine is particularly vulnerable thereto. Accordingly, it is generally considered useful to monitor side-product formation relative to dC in an effort to ensure that side-product formation is avoided or minimized.

Deprotection and cleavage are typically accomplished utilizing ammonia. Because of the widespread use of ammonia as a deprotection and cleavage reagent, it is conventional to compare other such reagents with ammonia in terms of the times necessary for deprotection and cleavage. Deprotection and cleavage by means of ammonia can require several days at room temperature, or between about 6 and 17 hours at 55° C. Typically, cleavage occurs within about 1 hour at room temperature, the remainder of the time being devoted to deprotection. The synthesis of a typical oligonucleotide (i.e. about 20–25 nucleotides in length) can be synthesized in about 2 hours; approximately six minutes is required to add one nucleotide to the insolubilized and growing nucleotide chain using most commercially available synthesizers. Relative to the time required to synthesize an oligonucleotide, the amount of time necessary to deprotect and cleave the oligonucleotide using ammonia can be excessive.

The use of different protection groups allows for a shortening of the time required for deprotection and cleavage. It has been reported that dimethylformamidine ("DMF") is a useful protection group for dG and dA. See Vu, Hugnh et al. "Fast oligonucleotide deprotection phosphoramidite chemistry for DNA synthesis". *Tetrahedron Letters,* 31:7269–7272 (1990) which is incorporated herein by reference. As described, oligonucleotides including such protection groups require 1 hour at 55° C. in aqueous ammonia, or 8 hours at room temperature in aqueous ammonia, for deprotection and cleavage. It has also been reported that phenoxyacetyl ("PAC") is a useful protection group for dG and dA. See, EPO Published Application 0241363 A1, "Derives de nucleotides et leur utilization pour la synthèse d'oligonucleotides", Molko, Didier et al (1987) which is incorporated herein by reference. As described, oligonucleotides including this protection group require between 2 to 8 hours at room temperature in aqueous ammonia for deprotection and cleavage.

An alternative approach to reduce the time required for deprotection and cleavage is to use other deprotection and cleavage reagents alone or in conjunction with ammonia. It has been reported that a reagent comprising a lower alkyl alcohol, water and a non-nucleophilic hindered alkylamine containing from 3 to 6 carbon atoms provides for cleavage within 1–2 hours at room temperature, followed by deprotection in about 20 to 60 minutes at about 80° C. to about 90° C. See EPO Published Application 0323152 A2, "Methods of Synthesizing Oligonucleotides", Woo, Sam Lee, et al (1989) (hereafter "Woo") which is incorporated herein by reference. Treatment of oligonucleotides with a 1:1 mixture (v/v) of n-butylamine/methanol for deprotection and cleavage has been described. See Weber, H. and Khorana, H. G. "CIV. Total synthesis of the structural gene for an alanine transfer ribonucleic acid from yeast. Chemical synthesis of an icosa-deoxynucleotide corresponding to the nucleotide sequence 21 to 40." *J. Mol. Biol.* 72:219–249 (1972) (hereinafter "Weber") which is incorporated herein by reference. However, this reagent is reported to have led to the formation of deoxycytidine side-products. Therefore, and as further described, oligonucleotides not containing cytidine where treated with a 1:1 mixture (v/v) of n-butylamine and methanol at room temperature for 2 days, and for oligonucleotides containing cytidine, treatment first included ammonia at room temperature for 2 days, (to avoid the formation of deoxycytidine side-products) followed by a 1:1 mixture (v/v) of n-butylamine and methanol at room temperature for 2 days.

The following is a brief summary of the described times necessary for deprotection and cleavage for the foregoing protecting groups and reagents:

| DEPROTECTION/CLEAVAGE TIMES | | |
| --- | --- | --- |
| REAGENT | TIME (HOURS) | TEMP (°C.) |
| Ammonia | 6–17 | 55 |
| Ammonia | >24 | R.T. |
| DMF/Ammonia | 2 | 55 |
| DMF/Ammonia | 8 | R.T. |
| PAC/Ammonia | 8 | R.T. |
| Woo* | 1–3 | R.T.; 80/90 |
| Weber** | 2 days | R.T. |
| Weber*** | 4 days | R.T. |

*mixture of lower alkyl alcohol, water, non-nucleophilic hindered alkylamine containing from 3–6 carbon atoms; 1–2 hours at R.T. (cleavage) and 20–60 minutes at 80–90° C. (deprotection)
**non-C containing oligonucleotides: 1:1 mixture (v/v) n-butylamine/methanol.
***oligonucleotide including C: ammonia (2 days) followed by n-butylamine/methanol (2 days).
R.T. = room temperature While certain of the foregoing reported reaction times for cleavage and deprotection are less than that of ammonia alone, it is evident that relative to the time necessary to synthesize an oligonucleotide, much time is devoted to deprotection and cleavage.

What is needed, given the rapidity in which oligonucleotides can be synthesized, is a reagent that can both rapidly remove the variety of available protection groups, and cleave the oligonucleotide from the support, with minimal to no side-product formation. From a practical perspective, it is preferred that such a reagent be useful across various temperatures, such that, in conjunction with the step of heating, the rapidity at which such a reagent can both deprotect and cleave an oligonucleotide is increased.

SUMMARY OF THE INVENTION

The present invention satisfies at least this need. In accordance with the invention disclosed herein, a reagent useful in the deprotection and cleavage of synthetically produced oligonucleotides is provided. The reagent comprises at least one straight chain alkylamine having from between 1 to about 10 carbon atoms. Preferably, the reagent additionally comprises at least one transamination suppression reagent, with t-butylamine being a particularly preferred transamination suppression reagent. The reagent can further comprise ammonia.

Preferably, the alkylamine of the reagent has from between 1 to about 6 carbon atoms, more preferably between 1 to about 3 carbon atoms, and most preferably, 1 carbon atom. Accordingly, a most preferred reagent comprises methylamine. Advantageously, deprotection and cleavage of oligonucleotides can take place at room temperature in less than about 90 minutes; however, higher temperatures may also be utilized to achieve faster deprotection of cleavage.

In accordance with the present invention, methodologies for cleaving a protected oligonucleotide, removing the protecting groups from a soluble oligonucleotide, and deprotecting an insolubilized oligonucleotide, in conjunction with the disclosed reagent, are possible.

These and other advantages will be made apparent as the disclosure proceeds.

BRIEF DESCRIPTION OF THE DRAWINGS

The following drawings are intended to be used for purposes of illumination of the Detailed Description of Preferred Embodiments.

DETAILED DESCRIPTION OF PREFERRED EMBODIMENTS

Figure 1:
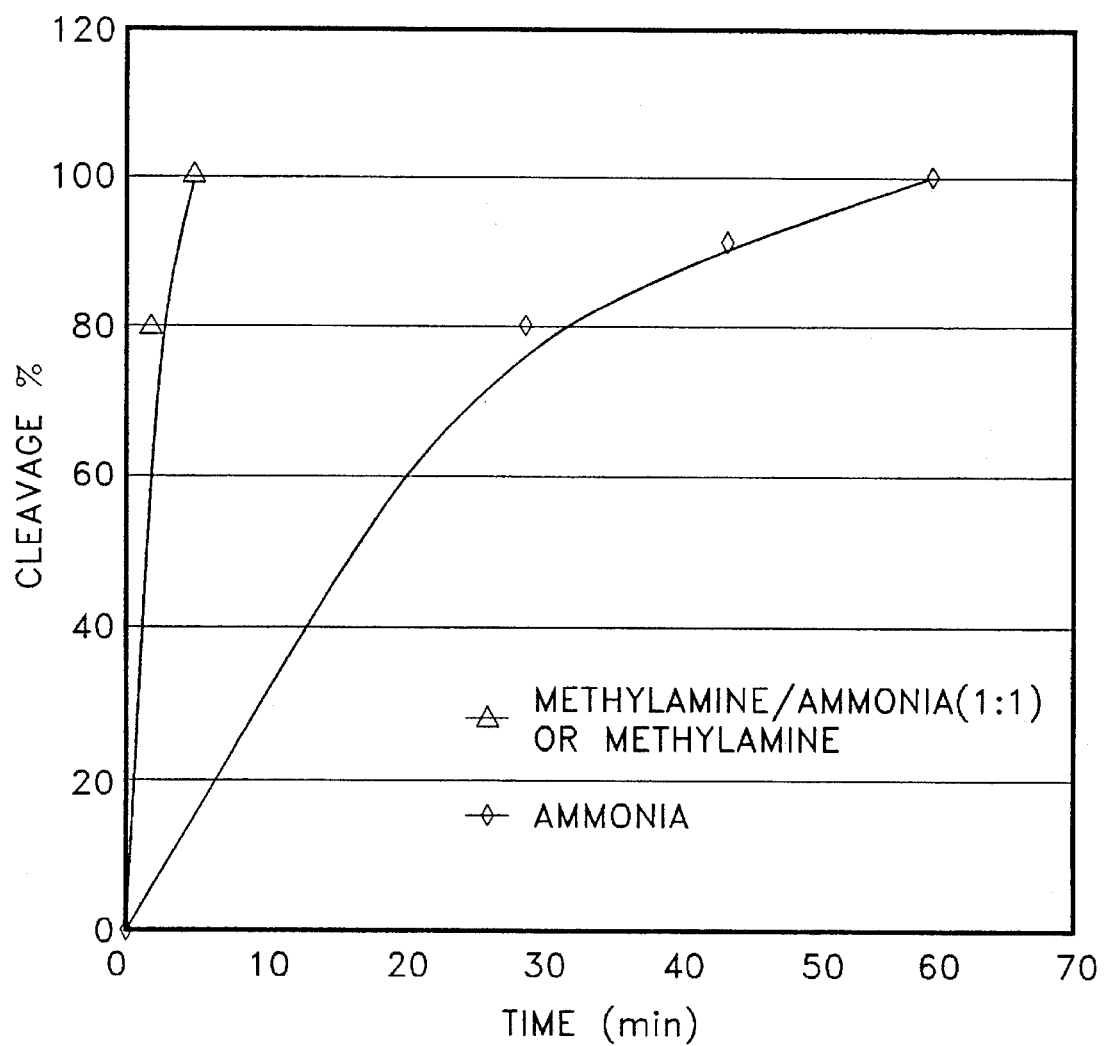
FIG. 1 is a graphic representation of the time for cleavage of insolubilized, heterogeneous 21-mers, using various reagents.

As those in the art appreciate, a drawback associated with automated synthesizers is the time necessary for deprotection of the protecting groups and, if synthesized on a solid support material, cleavage therefrom. Additionally, and from a practical perspective, for the majority of commercially available automated synthesizers that conduct cleavage and deprotection on the instrument itself, that instrument cannot be utilized during the cleavage step, which of course reduces throughput. Additionally, conventional cleaving and deprotecting agents can require an individual to manually push/pull ammonia through the synthesizer column to effectuate cleavage and deprotection, thus reducing the time that the individual could be engaged in other projects. Furthermore, heating of the contents of the synthesizer column with ammonia typically requires pouring the insolubilized oligonucleotide into a different container, adding ammonia, heating the new container, and centrifuging the container to remove the support material. All of these steps are inherently time consuming and add the potential for, inter alia, errors.

While a reagent which can reduce the time for deprotection and cleavage is of course an obvious goal, those in the art will appreciate that any such reagent must satisfy at least the following criteria: the integrity of the oligonucleotide must be preserved, i.e. the oligonucleotide must be biologically useful for e.g., use as probes, sequencing and synthesizing, etc.; and, side product formation must be substantially minimized, and, preferably, excluded altogether.

As used herein, the term "oligonucleotide" is meant to encompass synthetic deoxy- and ribo-oligonucleotides as well as modified oligonucleotides, i.e. where the 3'OH, 5'OH, sugar, or heterocyclic base are modified, as well as modification of the phosphate backbone (e.g. methyl phosphonates, phosphorothioates, and phosphoramidates). Additionally, oligonucleotides can also include oligonucleotides comprising an attached reporter group, e.g. biotin, avidin, haptens, dyes, fluorescent, chemiluminescent, enzymatic or radioactive labels, and solid supports other than the solid support from which the oligonucleotide is synthesized.

As used herein, the terms "rapid", "substantially shortened" "fast", etc. when used in relation to the disclosed reagent, are relative, and depend upon the temperature of the medium in which the reagent is operating. Broadly, these terms are intended to indicate that deprotection and cleavage can be completed within at least about 90 minutes at room temperature, and within at least about 15 minutes at about 90° C. Comparatively, ammonia requires at least about 24 hours at room temperature for cleavage and deprotection, and at least about 30 minutes at about 80° C.

It has been discovered that combinations of at least one first agent which is at least 5 times more nucleophilic than ammonia; at least one second agent that is at least 1.5 times less polar than water; and aqueous ammonia, can be effectively utilized as deprotection and cleavage reagents which substantially prevent transamination/side product formation. "Combinations", as used herein in reference to the first agent, the second agent, and aqueous ammonia, is meant to indicate that the reagent comprises at least the following preferred embodiments:

a) first agent;

b) first agent and aqueous ammonia;

c) first agent and second agent; and d) first agent; aqueous ammonia; and second agent.

The first agent (more nucleophilic than ammonia) is a straight chain alkylamine having from between 1 to about 10 carbon atoms. In addition to the nucleophilicity thereof, the length of the alkylamine is also a consideration, such that preferably, the straight chain alkylamine has from between 1 to about 6 carbon atoms, more preferably from between 1 to about 3 carbon atoms, and most preferably 1 carbon atom (i.e., methylamine). Methylamine is a particularly preferred first agent because it is about 40 times less nucleophilic than ammonia and because it is the "smallest" of the defined straight chain alkylamines. While not wishing to be bound to any particular theory, it is believed that such agents, due to their nucleophilicity and size, are particularly well suited to attack the bonds between the protecting groups (and the solid support, if utilized) and the individual nucleotides of the oligonucleotide. Because of the relative "ease" at which such agents can attack these bonds (i.e., increase in reaction kinetics), the time for deprotection and cleavage is substantially shortened.

As those in the art appreciate, "transamination" refers to the exchange of amines on a nucleotide; typically, transamination is manifested as side-product formation. In the presence of, e.g., methylamine, the potential for transamination of, e.g., cytidine to N-methylcytidine, an unwanted side-product, increases. Accordingly, it is preferred that the reagent comprises at least one second agent (less polar than water) as a transamination suppression agent (for convenience, hereinafter referred to as "TSA"). The TSA is preferably selected from the group consisting of straight-chain, branched, cyclic, saturated and unsaturated alkylamines having from between 1 and about 10 carbon atoms and which may further comprise functional groups; ethanol; methanol; isopropylamine; acetylnitrile, dimethylformamide; tetrahydrofuran; and combinations of the foregoing. Exemplary alkylamines as defined include, but are not limited to, t-butylamine, ethylamine, propylamine, isopropylamine, dimethylamine, diethylamine, trimethylamine and secondary butylamine. The preferred TSAs have a polarity index value that is at least about 1.5 times less than that for water (the polarity index value for water is about 10). While not wishing to be bound by any particular theory, it is believed that this feature of the TSA substantially reduces or prevents transamination from occurring, due to beneficial interactions between the TSA with the nucleotide amines or agents comprising amines involved in a transamination event.

Aqueous ammonia can be added to the reagent, although this is not a requirement. The presence or absence of aqueous ammonia in the reagent is principally discretionary with the investigator. In essence, aqueous ammonia does not significantly affect the reagent in terms of the cleavage and deprotection reactions; however, the presence of aqueous ammonia in combination with the first agent can increase the time necessary for deprotection by about 50%. Accordingly, although the reagent can comprise aqueous ammonia, preferably, the reagent does not include ammonia.

Preferred volume-to-volume ratios of the components of the reagent are as follows: for an embodiment of the reagent comprising a first agent and a TSA second agent, a preferred ratio is between about 9:1 to about 1:9, more preferably from between about 7:3 to about 3:7, and most preferably about 1:1; for an embodiment of the reagent comprising a first agent and aqueous ammonia, a preferred ratio is between about 9:1 to about 1:9, more preferably from between about 7:3 to about 3:7, and most preferably about 1:1; and for an embodiment of the reagent comprising the first agent, a TSA second agent, and aqueous ammonia, a preferred ratio for the three components is from between about 9-1:9-1:9- 1 to about 1-9:1-9:1-9, more preferably from between about 7-3:7-3:7-3 to about 3-7:3-7:3-7, and most preferably about 1:1:1.

The reaction temperature is principally dependent upon the needs of the investigator. I.e., the reaction temperature can range from between about 25° C. to about 100° C. (although higher and lower temperatures can be utilized as long as the integrity of the oligonucleotide is not significantly impacted whereby the resulting oligonucleotide has substantially limited utility). As those in the art appreciate, increasing the temperature of a chemical reaction typically increases the reaction kinetics thereof. Thus, when speed is a consideration (such as in a commercial setting where it is desirable that oligonucleotide throughput is high), it is preferred that the reaction temperature be above room temperature, preferably greater than about 50° C., and most preferably between about 65° and about 80° C. While such temperatures do not have a substantial impact upon the cleavage time, such temperatures can substantially decrease the time necessary for deprotection. However, it is to be understood that the reaction temperature can be at room temperature such that cleavage and deprotection is accomplished in less than about 90 minutes.

In accordance with the disclosure, a particularly preferred embodiment of the reagent comprises a 1:1 volume to volume ratio of methylamine and t-butylamine. A particularly preferred reaction temperature is about 65° C.; at this temperature, deprotection and cleavage of protected, insolubilized oligonucleotides can be accomplished in less than about 10 minutes.

EXAMPLES

The following Examples, directed to preferred embodiments of the invention are not intended, nor should they be construed to be, limitations on the disclosure or the claims to follow:

I. Materials and Methods

A. Reagents

1. Cleavage/Deprotection Reagent

All chemicals were at least of ACS grade. Ammonium hydroxide was obtained from Aldrich (Milwaukee, Wis.; Cat. No. 22, 122-8). Methylamine, 40 wt % solution in water, was obtained from Aldrich (Cat. No. M2,775-1), as was t-butylamine (Cat. No. B8, 920-5).

Methylamine/t-butylamine reagent was prepared by mixing a 1:1 volume-to-volume ratio, followed by shaking for 5 minutes at room temperature and storage at 4° C. Ammonium hydroxide was stored in accordance with supplier instructions.

2. Protected Deoxynucleosides

The following protected deoxynucleosides were obtained from Sigma Chemical Co. (St. Louis, Mo.):

a) $dA^{bz}$ (Cat. No. B 6130);

b) $dC^{bz}$ (Cat. No. B 5882);

c) $dC^{ibu}$ (Cat. No. I 6261); and d) $dG^{ibu}$ (Cat. No. I 6007).

Thymidine was obtained from Sigma (Cat. No. T 5018).

A novel protected deoxycytidine was also utilized for the Examples. It was determined that $dC^{bz}$ and $dC^{ibu}$ (the so-called "traditional" protected deoxycytidines), when used in conjunction with the disclosed reagent, could lead to side-product formation. The novel protected deoxycytidine comprises an acetyl ("Ac") protecting group. Synthesis thereof is disclosed in the co-pending application referenced above, which is incorporated fully herein by reference.

B. Commercially Available Protocols

1. Polymerase Chain Reaction ("PCR")

PCR analysis of oligonucleotide primers subjected to the disclosed cleavage/deprotection reagent was conducted using a Perkin Elmer Cetus GeneAmp™ DNA Amplification Reagent Kit with AmpliTaq™ (Part NO. N801-0055). Manufacturer instructions were followed.

2. DNA Sequencing

Sequencing reaction was performed using M13mp18 single stranded DNA template (New England Biolabs, Cat. No. 404-C) following the protocol of United States Biochemical Sequenase® Version 1.0, using $\alpha$-[$^{35}$S]-dATP.

C. Instruments

1. Automated DNA Synthesizer

Synthesis of oligonucleotides was performed using a Biosearch 8750™ DNA synthesizer; controlled pore glass (CPG), 500Å–1000Å pore size, was used for the solid support material. Homo- and hetero-oligonucleotides of various lengths were synthesized in accordance with manufacturer instructions.

2. Capillary Electrophoresis

Capillary electrophoresis of oligonucleotides was performed on a Beckman Instruments, Inc. P/ACE™ 2000 high performance capillary electrophoresis system. A 37 cm U100P Urea Gel Column (Beckman, Cat. No. 338480) was utilized. Samples were loaded onto the columns via the electrokinetic injection method (10 kV, 3 seconds); separation was conducted at 11 kV/cm for 30–90 minutes, depending on oligonucleotide length. Tris-hydroxymethyl aminomethane ("TRIS")-borate 7M urea, running buffer (Beckman, Gel Buffer Kit, Cat. No. 338481) was utilized. Absorbance detection was in the range of from 0.05 to 2.0 $OD_{260\ nm}$/ml, depending principally on the length of the oligonucleotide.

3. High Pressure Liquid Chromatography ("HPLC")

HPLC analysis was conducted on a Beckman Instruments System Gold™ HPLC Programmable Solvent Module 126 equipped with a diode array detector module 168 and autosampler 507. A $C_{18}$ Ultrasphere™ HPLC column (Beckman, Cat. No. 235329; 5 µ particles, 4.6mm×25cm) was utilized. Bottle A contained 0.1M ammonium acetate, pH 6.9; Bottle B contained HPLC-grade acetonitrile. The system was operated in a gradient mode as follows (1 ml/min. flow rate): 0–10 min: 85% Bottle A, 15% Bottle B; 20–25 min: 75% Bottle A, 25% Bottle B; 25–27 min: 50% Bottle A, 50% Bottle B; 27–30 min: 50% Bottle A, 50% Bottle B; 30–35 min, 100% Bottle A, 0% Bottle B.

II. Example I. Cleavage of Support-Bound, Protected Oligonucleotides

Heterogeneous 21-mers were synthesized using the Biosearch 8750 synthesizer. Four different types of 21mers were analyzed, whereby each of the four nucleosides were tethered to the support, (i.e., the site of cleavage); the remaining 20 nucleosides were identical. Accordingly, the disclosed reagent was evaluated for cleavage time for each of the four nucleosides.

For comparative purposes, the following conditions were analyzed.

a) methylamine/t-butylamine (1:1, v/v);

b) methylamine; and d) ammonia.

Support bound oligonucleotides were treated with 1 ml of the foregoing reagents by passing the reagents back-and-forth through the column comprising the oligonucleotides via syringes placed on either end of the column, at room temperature. Aliquots (50 µl) of the resulting mixtures were removed at 1, 2, 5, 10, 15, 30 and 60 minutes, admixed with 1 ml double-distilled $H_2O$ and absorbance was measured at 260nm.

Irrespective of the nucleoside immediately adjacent to the solid support, cleavage was accomplished in about 5 minutes for reagents (a) and (b) above. For ammonia, cleavage was accomplished in about 60 minutes for all conditions. FIG. 1 provides a kinetics plot summarizing the preceding, as a percentage of cleavage of the oligonucleotides over time.

Example II: Deprotection of Protected Oligonucleotides

Deprotection of protected oligonucleotides was determined by reverse-phase HPLC analysis of enzymatically digested oligonucleotides. Enzymes utilized were: (1) phosphodiesterase I (Sigma, Cat. No. P-689F) reconstituted with 5 ml of 40 mM TRIS, and 10 mM $MgCl_2$, pH 7.5 (0.01 U was utilized per assay); and, (2) alkaline phosphatase (Sigma, Cat. No. P-4252) from E. coli 200 U/1.8 ml (0.2 U was utilized per assay). 25 µl of phosphodiesterase and 2 µl of phosphatase were added to 1–2 $OD_{260nm}$ of oligonucleotide, followed by incubation at room temperature for 30 minutes to 120 minutes. 0.5 to 1.0 $OD_{260nm}$ of the digested mixture was injected onto the above-referenced HPLC column.

Because deprotection of protected deoxyguanosine is the rate limiting step, analysis of several 21-mer oligonucleotides consisting of different percentages of $dG^{ibu}$ were investigated. Synthesis was conducted using the above-referenced DNA synthesizer to produce the following 21-mers:

1) 5'-CTG-GAC-AGT-AGT-CAG-ACT-GC-(T)-3' [25% G]
2) 5'-GTG-GAC-GCT-AGG-GCG-GAG-(C-(T)-3' [50% G]
3) 5'-Gx21-3' [100% G]

The tested reagents were the same as presented in Example I. Reaction temperatures ranged from 25° to 80° C. Results are as follows in Table I:

TABLE I

Deprotection of Protected Oligonucleotides (time, in minutes)

| Temperature (°C.) | Methylamine/ t-butylamine | | | Methylamine/ Ammonia | | |
|---|---|---|---|---|---|---|
| | 25% G | 50% G | 100% G | 25% G | 50% G | 100% G |
| 25 | 75 | 90 | 90 | 75 | 75 | 100 |
| 37 | 20 | 30 | 30 | 20 | 30 | 30 |
| 55 | 7 | 10 | 10 | 10 | 10 | 10 |
| 65 | 5 | 5 | 7 | 10 | 7 | 5 |
| 80 | 2 | 3 | 3 | 2 | 2 | 2 |

| Temperature (°C). | Methylamine | | | Ammonia | | |
|---|---|---|---|---|---|---|
| | 25% G | 50% G | 100% G | 25% G | 50% G | 100% G |
| 25 | 60 | 60 | 60 | 4320 | 4320 | 5940 |
| 37 | 20 | 20 | 20 | 1200 | 1200 | 1800 |
| 55 | 5 | 7 | 7 | 240 | 240 | 360 |
| 65 | 5 | 5 | 5 | 180 | 180 | 240 |
| 80 | 2 | 2 | 2 | 60 | 60 | 90 |

The foregoing data illustrates a variety of features of the disclosed reagent. Initially, it is noted that relative to ammonia, the so-called "traditional" cleavage/deprotection reagent, the disclosed reagent performs both cleavage and deprotection in significantly shorter times. Additionally, it is noted that as temperature increases, the reaction kinetics also increase, as evidenced by the decrease in deprotecting times. Thus, it is possible to utilize the disclosed reagent across a variety of reaction temperatures, depending upon the needs of the investigator. Furthermore, it is noted that in terms of cleavage and deprotection, not only do various embodiments of the disclosed reagent function on an approximate equivalent par, the various embodiments perform significantly better than the traditional cleavage/deprotection reagent.

Example III: Cytidine Side Product Formation

As noted, deoxycytidine is ordinarily most susceptible to side product formation during, e.g., deprotection of oligonucleotides comprising deoxycytidine. Typically, such side product formation is via transamination during the deprotection step or after deprotection when the reagent continues to be in contact with the deprotected deoxycytidine.

As those in the art appreciate, the synthesis of oligonucleotides is typically conducted with the intent of retrieving the end-product as quickly as possible. Occasionally, however, it is possible that the solubilized, protected oligonucleotide may remain in a deprotection reagent for extended time periods. As those in the art further appreciate, such an increase in time when the oligonucleotide is within the reagent can increase the chance of a transamination event, thus increasing the chance of side product formation.

Deoxycytidine side product formation was investigated by reverse phase HPLC, using both methylamine and methylamine/t-butylamine as the reagent, across several times and temperatures. The "traditional" deoxycytidine protecting groups, "bz" and "ibu" were studied, as well as the above-referenced "Ac" protecting group. The side product observed when utilizing such reagent (as confirmed by Nuclear Magnetic Resonance) was N-methyl cytidine. Percentage of N-methyldeoxycytidine formation, relative to deoxycytidine, are presented below, based upon solution-based deprotection of deoxycytidine protected with an Ac protecting group:

TABLE II

Percentage of N-methylcytidine Formation*

| Reagent | TEMPERATURE | | |
|---|---|---|---|
| | 25° C. | 37° C. | 65° C. |
| Methylamine | <0.01** (60 min.) | <0.01 (20 min.) | <0.01 (5 min.) |
| Methylamine (16 hrs.) | ~0.05 | ~0.25 | ~2.5 |
| Methylamine/ t-butylamine (16 hrs.) | <0.01 | <0.01 | ~0.6% |

*average percentages
**0.01% is the lowest detectable limit of the instrument

These results indicate that for a typical oligonucleotide synthesis (i.e. one in which the investigator is desirous of obtaining the finished end product as soon as possible), a reagent comprising mehtylamine does not lead to statistically significant cytidine side product formation. However, as the time that the oligonucleotide remains in the reagent increases, so too does the formation of cytidine side product formation. Thus, the use of a Transamination Suppression Reagent, (as defined) is useful; the data indicates that relative to methylamine, a reagent comprising methylamine and the TSA t-butylamine significantly reduces cytidine side product formation.

Beneficially, then, a TSA can be included in the reagent whether or not such extended reaction times are contemplated. As should be appreciated, the use of a TSA, although ordinarily not ,necessary, is preferred for at least two reasons: first, the presence of the TSA reduces the potential for side product formation; and second, the investigator is provided with the opportunity to maintain the oligonucleotide within the reagent for periods in excess of optimal cleavage/deprotection times, if such extended time periods are desired.

A secondary set of studies was conducted along these lines. For these studies, side product formation for $dC^{Ac}$, $dC^{ibu}$, $dC^{bz}$, $dG^{ibu}$, $dA^{bz}$ and dT (as a relative percentage of non-side product formation for the nucleosides) were investigated at various times and temperatures using methylamine/t-butylamine as the reagent. Results are as presented in Table III:

TABLE III

Percentage of Side Product Formation*

| Temp. (°C.) | Reaction Time | $C^{AC}$ | $C^{ibu}$ | $C^{bz}$ | $G^{ibu}$ | $A^{bz}$ | T |
|---|---|---|---|---|---|---|---|
| 25 | 90 min. | ** | 0.15 | 10.0 | ** | ** | ** |
| 25 | 16 hrs. | ** | *** | *** | ** | ** | ** |
| 37 | 30 min. | ** | 0.15 | 10.0 | ** | ** | ** |
| 37 | 5 hrs. | ** | *** | *** | ** | ** | ** |
| 37 | 16 hrs. | ** | *** | *** | ** | ** | ** |
| 65 | 5 min. | ** | 0.15 | 10.0 | ** | ** | ** |
| 65 | 1 hr. | ** | *** | *** | ** | ** | ** |
| 65 | 16 hrs. | 0.6 | *** | *** | ** | ** | ** |
| 80 | 3 min. | ** | 0.15 | 10.0 | ** | ** | ** |
| 80 | 1 hr. | *** | *** | ** | ** | ** | ** |

*Averages
**<0.01
***not investigated due to high percentages at optimal temperature/reaction time These results indicate at least several things. First, with respect to the dC protection groups, the data indicates that an "Ac" protecting group can beneficially be utilized in conjunction with the disclosed reagent; the "traditional" cytidine protecting groups resulted in significantly higher side product formation. Second, the disclosed reagent does not lead to statistically significant side product formation for any of the protected deoxynucleosides at any of the investigated temperatures or reaction times, with the exception of deprotection of $dC^{Ac}$ at the elevated temperatures and at times greater than the desired reaction times. Thus, for oligonucleotides comprising deoxycytidine protected with an Ac protecting group, it is preferred that at such elevated temperatures, extended reaction times not be utilized.

Example IV: Enzymatic Digestion Analysis of Non-Purified Oligonucleotides

Analysis of the composition of several oligonucleotides were conducted using enzymatic digestion and reverse phase HPLC techniques. These studies were conducted using deoxycytidines protected with an Ac protecting group and a traditional protecting group, bz; all other protecting groups were consistent between the oligonucleotides. 35-mers, 51-mers and 101-mers, having the following sequences, where analyzed:

35-mer

5'-CAG—TGC—AGC—TCC—TAG—CAG—CCT—AGC—GTA—CTA—GTC—TT-3'

51-mer

5'-CAG—TCC—TAG—TCA—CAG—TCC—AGT—CGC—TCA—AGC—GTC—CAG—

TTG—CAC—AGG—TCA—CCT-3'

101-mer

5'-GCT—GCC—AGT—TCG—GTC—ATC—CGA—TCC—TCG—GTC—ACG—CAA—
CTG—TCA—ACG—GCA—CCT—ACT—CCT—CGT—AAC—GTA—GGA—CAG—TCC—
GAT—TCG—CAC—GTG—CAA—AGC—CCA—TTC—AT-3'

The oligonucleotides were cleaved and deprotected using an embodiment of the reagent comprising methylamine/t-butylamine at 25° C. for 90 minutes or ammonia for 3 hrs. at 65° C.; solubilized, deprotected oligonucleotides were not purified prior to analysis. Results are as follows in Table IV:

TABLE IV

| | | | Composition Analysis | |
|---|---|---|---|---|
| | | | Determined | |
| | | Theoretical | Oligonucleotides Comprising $dC^{Ac}$ | Oligonucleotides Comprising $dC^{bz}$ |
| 35-mer | C | 11 | 10.67 | 10.62 |
| | G | 8 | 7.88 | 7.84 |
| | T | 9 | 9.65 | 9.41 |
| | A | 7 | 6.80 | 7.13 |
| 51-mer | C | 18 | 17.04 | 17.36 |
| | G | 11 | 11.71 | 11.72 |
| | T | 11 | 11.61 | 11.07 |
| | A | 11 | 10.65 | 10.85 |
| 101-mer | C | 35 | 33.80 | 33.53 |
| | G | 22 | 20.74 | 20.70 |
| | T | 22 | 21.78 | 21.73 |
| | A | 22 | 25.09 | 25.04 |

The theoretical composition of the various non-purified oligonucleotides and the determined composition provide good correlation. Additionally, the difference in deoxycytidine protecting groups, based upon the above data, does not indicate a statistically significant difference in results.

Example V. Melting Point Determination

Melting point determinations were derived for a heterogeneous 21-mer and the complement thereof; identical oligonucleotides, cleaved and deprotected with either the disclosed reagent comprising methylamine/t-butylamine, or ammonia, when investigated. The 21-mer, and the complement thereof, had the following sequences:

21-mer

5'-AGC-TAC-GGT-CAT-CGT-ATG-CAT-3'

Complement

5'-ATG-CAT-ACG-ATG-ACC-GTA-GCT-3'

Oligonucleotides were subjected to an embodiment of the reagent comprising methylamine/t-butylamine, for 90 min. at 25° C., or ammonia for 3 hrs. at 65° C. After deprotection and cleavage, 0.5 $OD_{260nm}$ (in 20 μl minimum volume) of each oligonucleotide and its complement were added to 1 ml of 10 mM TRIS, pH 7.5. Samples were boiled for 10–15 minutes, followed by slow heating on a lead heating block. Samples were placed in a cuvette, and absorbance (260 nm) was followed from 25° C. to 70° C. by raising the cuvette temperature at 3° C. intervals, followed by 3 minutes for stabilization and absorbance reading. Results are presented in FIG. 2, where "." are the readings for the ammonia-treated oligonucleotides, and "*" are the readings for the disclosed reagent treated oligonucleotides.

Figure 2:
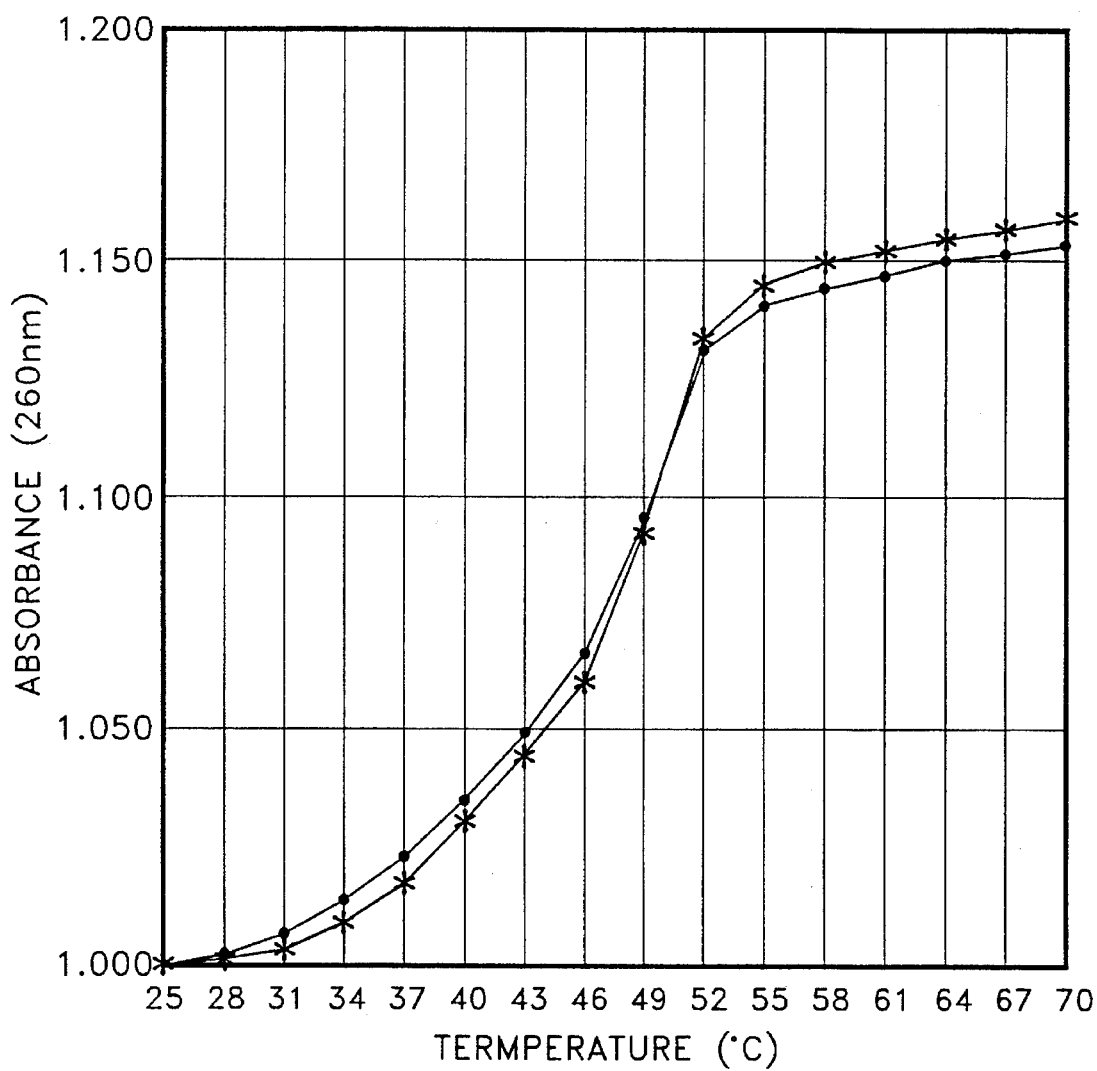
FIG. 2 is a melting point analysis of a 21-mer (and its complement) subjected to methylamine/t-butylamine as a cleavage/deprotection reagent, and ammonia as a cleavage/deprotection reagent.

The results presented in FIG. 2 indicate that the disclosed reagent, vis-a-vis ammonia, did not affect the melting point temperature of the 21-mer. Absorbance readings versus temperature followed a nearly identical pattern under both reagent conditions.

Example VI. Polyacrylamide Gel Electrophoresis ("PAGE")

Analysis of 35-mers (35% $dC^{bz}$; 35% $dC^{Ac}$; 100% $dC^{bz}$; and 100% $dC^{Ac}$), 51-mers (35% $dC^{bz}$; 35% $dC^{Ac}$; 100% $dC^{bz}$; and 100% $dC^{Ac}$); and 101-mers (35% $dC^{bz}$; 35% $dC^{Ac}$; 100% $dC^{bz}$; and 100% $dC^{Ac}$) were analyzed by PAGE. The hetero 35-, 51- and 101-mers were as described in Example IV and for the homo 35-, 51- and 101-mers, the oligomer was synthesized from an insolubilized thymidine. Oligonucleotides comprising $dC^{Ac}$ were cleaved and deprotected using a reagent comprising methylamine/t-butylamine for 90 min. at 25° C.; oligonucleotides comprising $dC^{bz}$ where cleaved and deprotected using ammonia for 3 hrs. at 65° C.

A 22 cm×16.5 cm denaturing gel was prepared by adding 107.3 ml of deionized water to 100 gm of premixed acrylamide/methylene bis-acrylamide (29:1) (Boehringer Mannheim Biochemicals, Indianapolis, Ind.; Cat. No. 100-151) to achieve a 50% stock solution. To 20 ml of the 50% stock solution was added 22.5 g urea, 5 ml of 10×Tris-Borate/EDTA ("TBE") and sufficient deionized water to achieve 50 ml. The solution was stirred and heated such that the solid constituents were dissolved. Thereafter, 20 mg ammonium persulfate and 20 µl N,N,N',N'-Tetramethyl ethylene diamine ("TEMD") was added; this solution was poured into clean plates and allowed to polymerize for 1 hr. gels when pre-run with 1×TBE at 20 mA for 1 hr. 0.2–1.0 $OD_{260nm}$ of each oligonucleotide was added to 10 µl of 10 m urea. The 20 µl admixtures were loaded onto the gel and electrophoresed at 28 mA for 2–4 hours, depending on the length of the oligonucleotide. Bands were visualized by UV shadowing on TLC fluorescent plate or by ethidium bromide staining.

Photographic results are presented in FIG. 3, where the lanes are defined as follows:

| Lane | Oligonucleotide |
|---|---|
| 1 | 35-mer (35% $dC^{Ac}$) |
| 2 | 35-mer (35% $dC^{bz}$) |
| 3 | 35-mer (100% $dC^{Ac}$) |
| 4 | 35-mer (100% $dC^{bz}$) |
| 5 | 51-mer (35% $dC^{Ac}$) |
| 6 | 51-mer (35% $dC^{bz}$) |
| 7 | 51-mer (100% $dC^{Ac}$) |
| 8 | 51-mer (100% $dC^{bz}$) |
| 9 | 101-mer (35% $dC^{Ac}$) |
| 10 | 101-mer (35% $dC^{bz}$) |
| 11 | 101-mer (100% $dC^{Ac}$) |
| 12 | 101-mer (100% $dC^{bz}$) |

Figure 3:
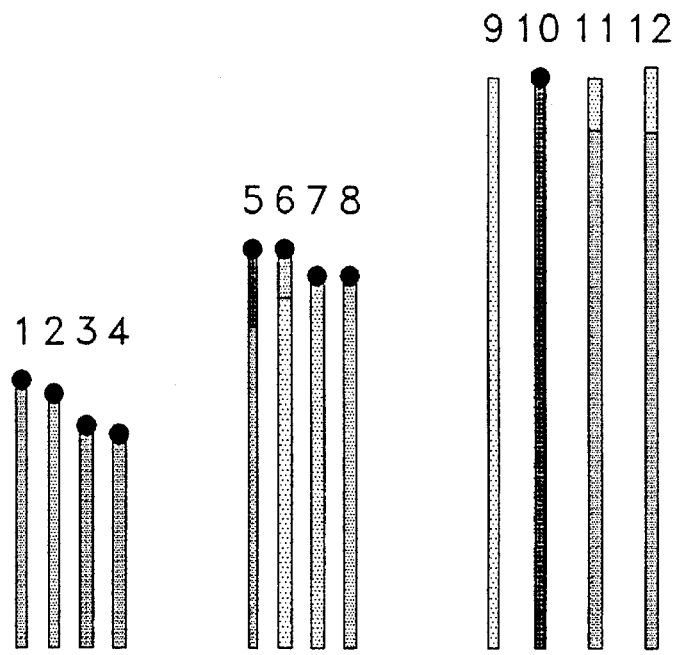
FIG. 3 is a photographic reproduction of a polyacrylamide gel electrophoresis analysis of various 35-, 51- and 101-mers comprising various percentages of $dC^{Ac}$ and $dC^{bz}$ and subjected to the cleavage/deprotection reagents of FIG. 2.

The results of FIG. 3 indicate that the oligonucleotides subjected to an embodiment of the disclosed reagent and the Ac protection group provided nearly identical PAGE patterns compared to the oligonucleotides subjected to ammonia and the traditional deoxycytidine protecting group, bz.

Example VII. Capillary Electrophoresis

Heterogeneous 51-mer oligonucleotides comprising either 35% $dC^{bz}$ or 35% $dC^{Ac}$ were subjected to either ammonia for 3 hrs. at 65° C. or methylamine/t-butylamine for 90 min at 25° C., respectively, and were analyzed by capillary electrophoretic techniques. Electropherograms for the oligonucleotide subjected to ammonia and an embodiment of the disclosed reagent, are presented in FIG. 4 and 5, respectively.

Figure 4:
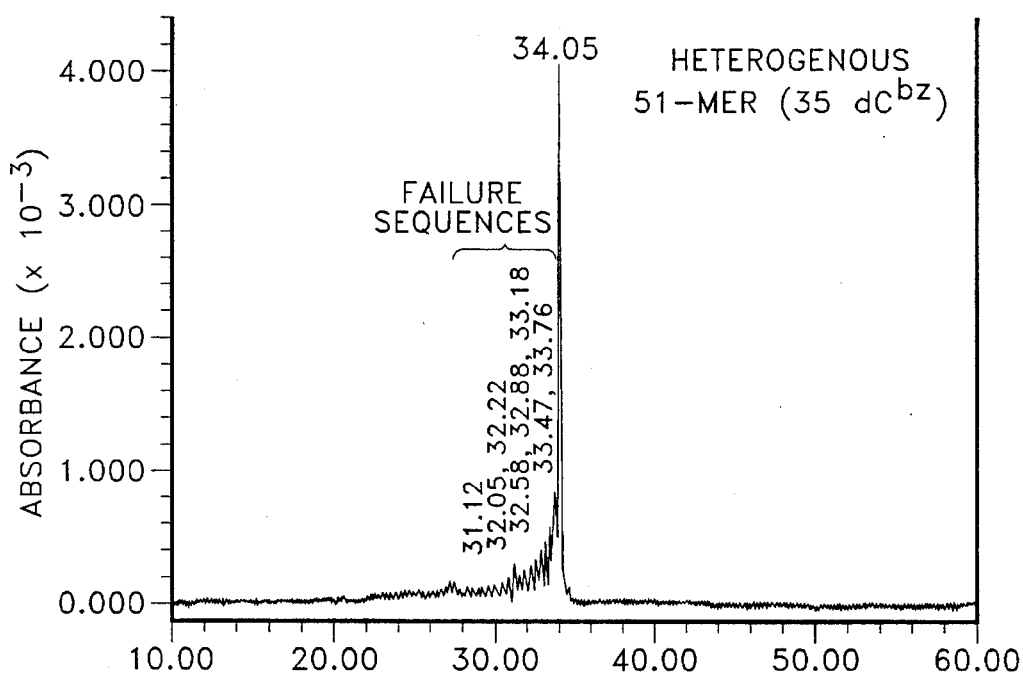
FIG. 4 is an electropherogram of a heterogeneous 51-mer comprising 35% $dC^{bz}$ subjected to ammonia as a cleavage/deprotecting reagent.
Figure 5:
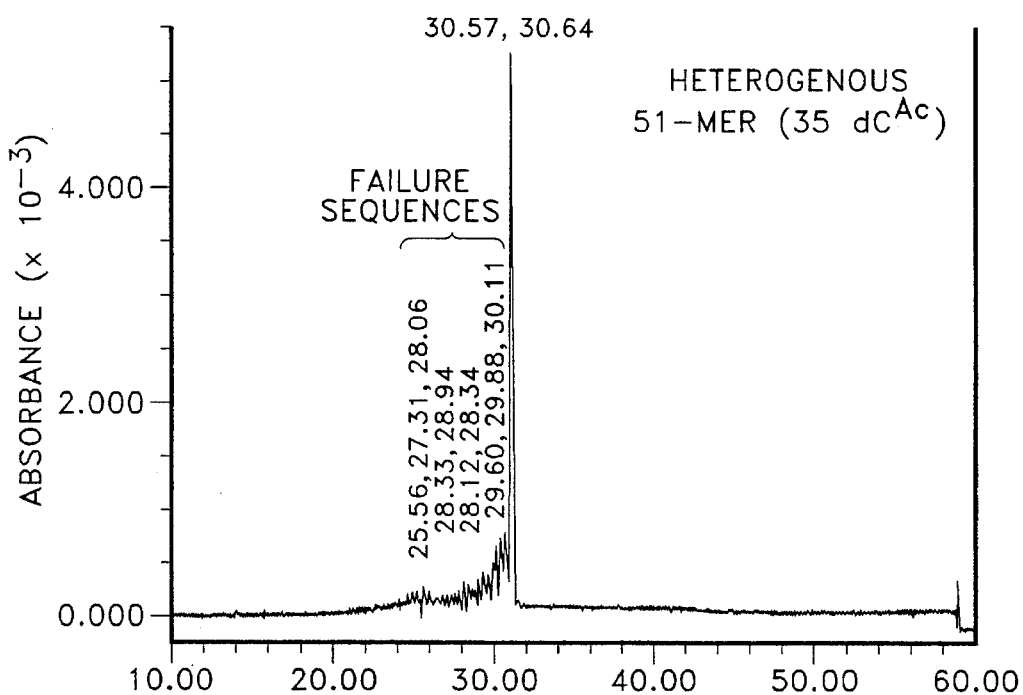
FIG. 5 is an electropherogram of a heterogeneous 51-mer comprising 35% $dC^{Ac}$ subjected to methylamine/t-butylamine as a cleavage/deprotection reagent.

The results of FIGS. 4 and 5 are nearly identical in terms of time from sample introduction to detection of the 51-mer. The percent-of-total integrated areas beneath the major peaks, 66.902 for FIG. 4 and 66.575 for FIG. 5, are also nearly identical. These results further indicate that the reagent and the Ac deoxycytidine protecting group provide comparatively identical soluble, deprotected oligonucleotides vis-a-vis ammonia and the traditional deoxycytidine protecting group, bz.

Example VIII. Polymerase Chain Reaction

The foregoing Examples evidences that the disclosed reagent can be utilized to rapidly and efficiently cleave and deprotect oligonucleotides. As those skilled in the art appreciate, however, it is necessary to be able to utilize such oligonucleotides for a variety of procedures.

Oligonucleotides used as primers in a polymerase chain reaction where generated and subjected to an embodiment of the disclosed reagent comprising methylamine/t-butylamine (where the deoxycytidines were protected with Ac) for 90 min. at 25° C. The primers were as follows:

18-mer

5'-CGC-CAG-GGT-TTT-CCC-AGT-3'

22-mer

5'-TTC-TGG-CGT-ACC-GTT-CCT-GTC-T-3'

The template was M13mp18 RFI DNA (New England Biolabs, Cat. No. 400-18). Manufacturer instructions were followed using the GeneAmp Reagent kit.

Initial melting temperature was 95° C. for 7 min.; 25 cycles were run on a Perkin Elmer Cetus DNA Thermal Cycler with the following cycle profile:

| | Temp. (°C.) | Time (sec) |
|---|---|---|
| Seq. #1 | 94 | 1 |
| Seq. #2 | 94 | 60 |
| Seq. #3 | 37 | 1 |
| Seq. #4 | 37 | 120 |
| Seq. #5 | 72 | 1 |
| Seq. #6 | 72 | 180 |

The resulting 957 base-pair PCR product was electrophoresed on a 1% agarose gel in TRIS-Acetate/EDTA ("TAE") and stained with ethidium bromide. Photographic results are presented in FIG. 6 where the designated lanes are as follows:

| Lane 1 | 957 bp product | (primers derived using methylamine/t-butylamine reagent and acetyl protecting group for deoxycytidine); |
|---|---|---|
| Lane 2 | 957 bp product | (primers derived using ammonia and bz protecting group for deoxycytidine); |
| Lane 3 | Gel Marker | (Lambda DNA digested with Hind III, 2322 and 2027 bp markers); and |
| Lane 4 | Gel Marker | (PBR322 DNA digested with Hinf I, 1632 and 506 bp marker) |

Figure 6:
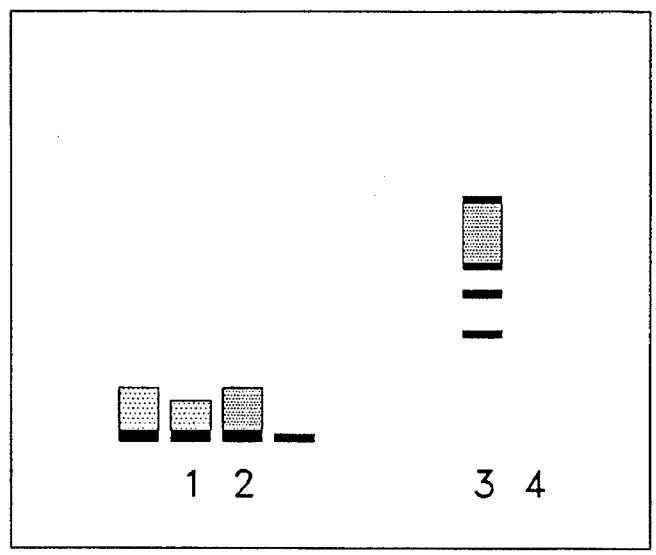
FIG. 6 is a photographic reproduction of PCR-derived 957 base-pair amplified template.

The results presented in FIG. 6 indicate that primers derived utilizing an embodiment of the disclosed reagent and deoxycytidine protecting group, Ac, led to the production of an amplified product substantially identical to that derived from primers generated by ammonia cleavage and deprotection and using a bz protecting group for deoxycytidine.

Example IX. DNA Sequencing

Two sets of 18-mers were synthesized using the deoxycytidine protecting group, Ac, and bz, and were subjected to an embodiment of the disclosed reagent comprising methylamine/t-butylamine for 90 min. at 25° C., and ammonia for 3 hrs. at 65° C., respectively. The 18-mers had the following sequence:

18-mer

5'-CGC-CAG-GGT-TTT-CCC-AGT-3'

Solubilized, deprotected oligomers were purified using Sep Pak (Waters, Part No. 5190) DNA purification kit. These purified oligomers were used as primers for sequencing purposes. The template was M13mp18 single stranded DNA (New England Biolabs, Cat. No. 404-C); sequencing was accomplished using the 18-mers in conjunction with the USB Sequenase materials and protocols. Results are presented in FIG. 7.

Figure 7:
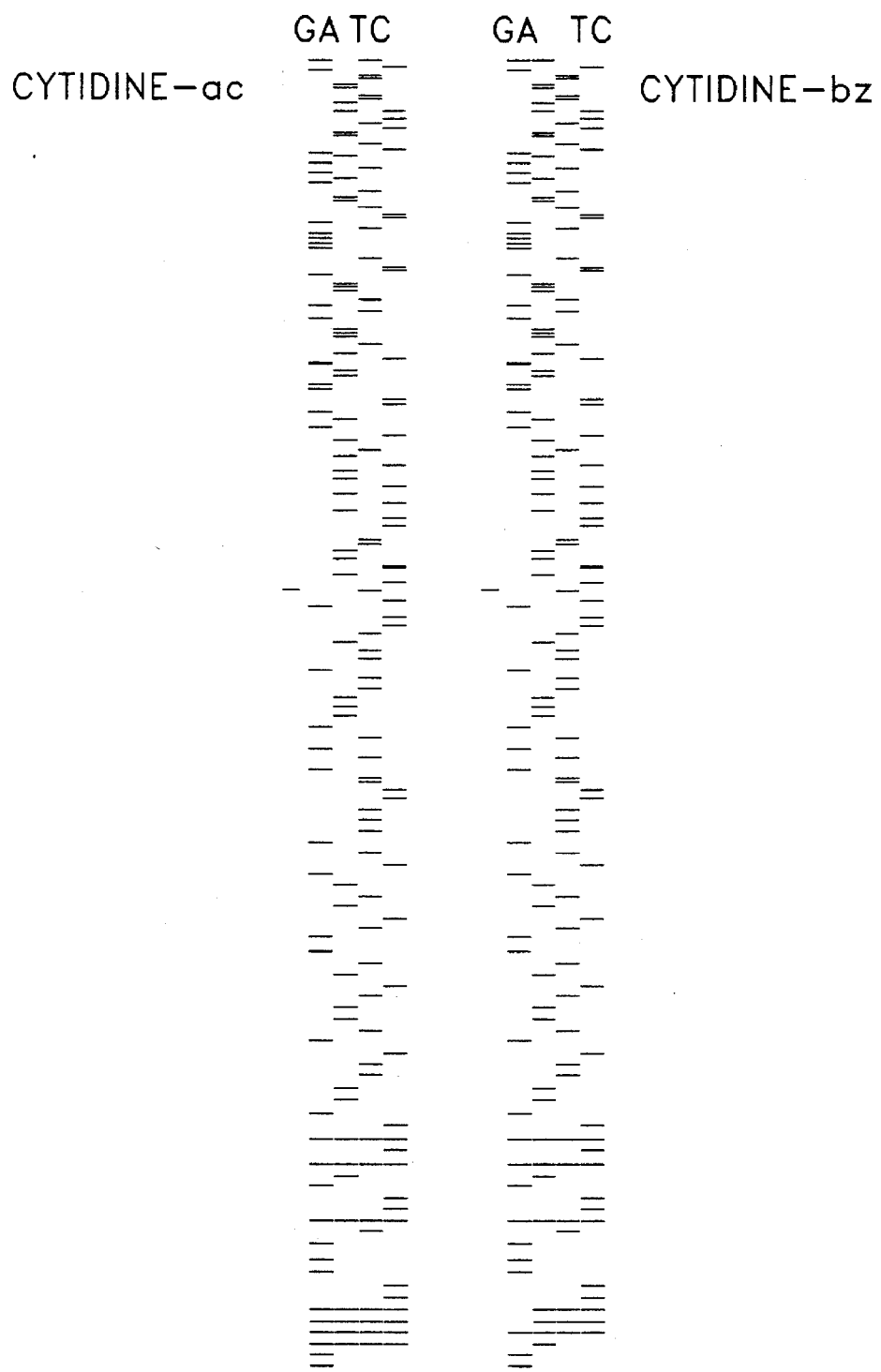
FIG. 7 is a photographic reproduction of a sequencing reaction of an M13mp18 template.

As the results of FIG. 7 indicate, the sequencing band patterns are substantially identical using primers subjected to the disclosed reagent and Ac protecting group vis-a-vis primers derived via ammonia and bz.

Example X. 3' Terminal Transferase Extension 22-mers were synthesized using the deoxycytidine protecting group, Ac, and bz, and were subjected to an embodiment of the disclosed reagent comprising methylamine/t-butylamine for 90 min. at 25° C., and ammonia for 3 hrs. at 65° C., respectively. The 22-mers had the following sequence:

22-mer

5'-TTC-TGG-CGT-ACC-GTT-CCT-GTC-T-3'

Solubilized, deprotected oligomers were purified using Sep Pak DNA purification kit. These purified oligomers were used as primers for 3' terminal transferase extension studies.

2.5 $OD_{260nm}$ of each oligonucleotide was added to 150 µl of deionized water; 5 mg Thymidine triphosphate ("TTP"), Sigma, Cat. No. T8635); 5 µl terminal deoxynucleotidyl transferase, 15 U/µl (BRL, Cat. No. 8008SB) and 50 µl trailing buffer. The admixture was incubated overnight at 37° C. and the resulting material purified using a Sep Pak $C_{18}$ cartridge as follows: the reaction mixture was diluted 1:2 in 0.5 m ammonium acetate, loaded onto the cartridge, followed by washing of the cartridge with deionized water, and the product eluted with 60% methanol in deionized water. The products were analyzed by capillary electrophoresis; electropherogram results are presented in FIGS. 8 and 9.

Figure 8:
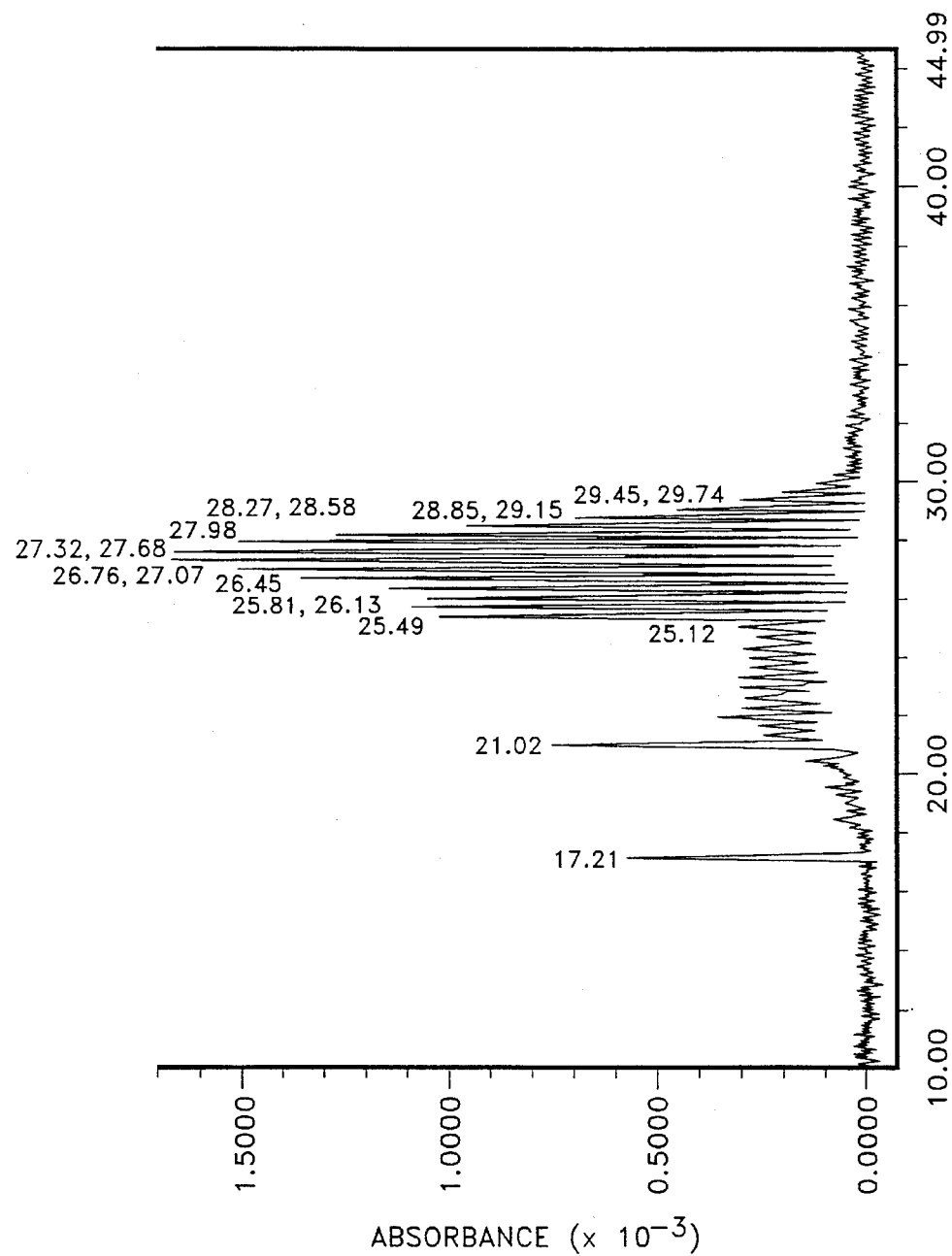
FIG. 8 is an electropherogram of a 3'-Terminal Transferase extension initiated using a 22-mer comprising $dC^{Ac}$ and subjected to methylamine/t-butylamine as a cleaving/deprotecting reagent.
Figure 9:
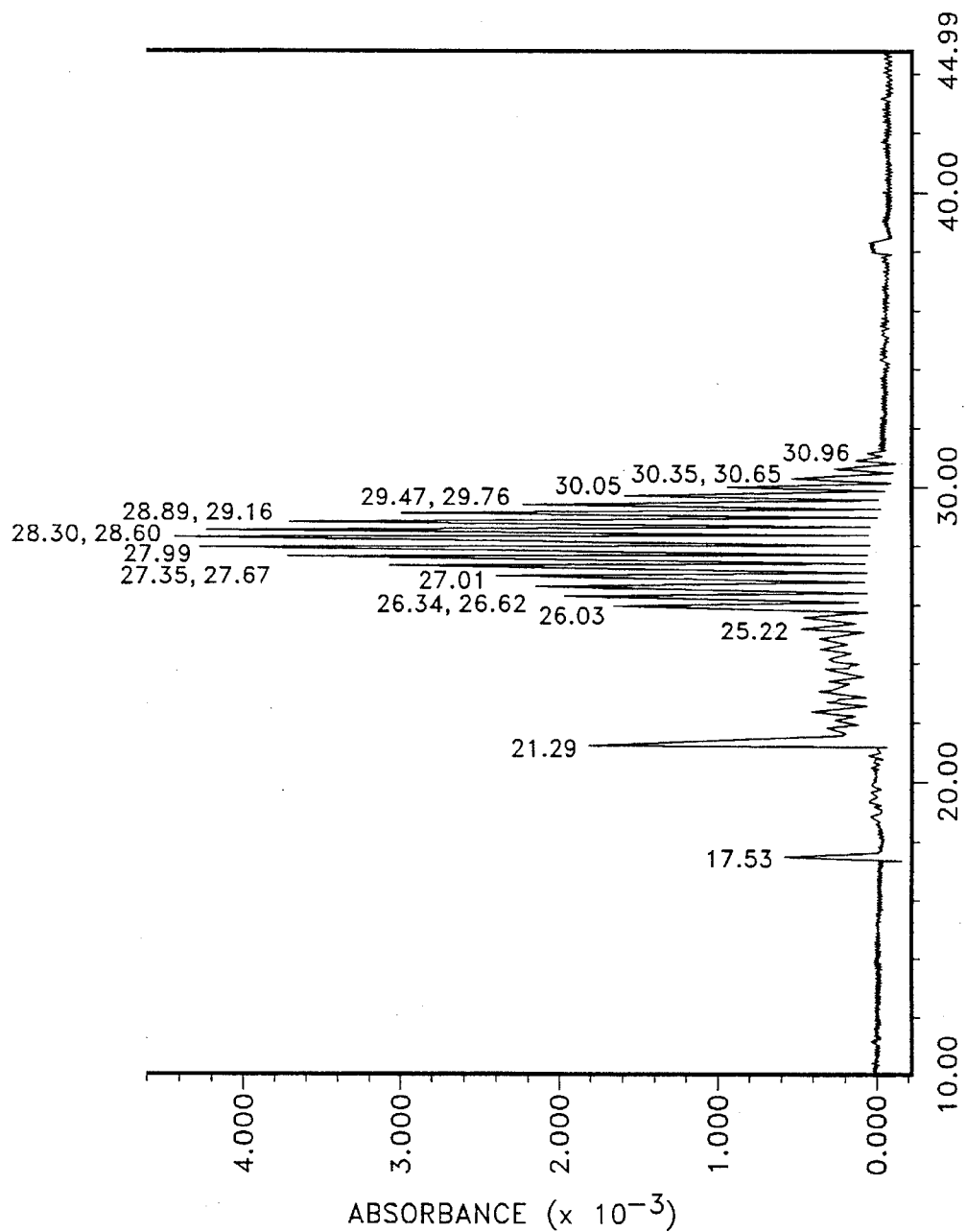
FIG. 9 is an electropherogram of a 3'-Terminal Transferase extension initiated using a 22-mer comprising $dC^{bz}$ and subjected to ammonia as a cleaving/deprotecting reagent.

The electropherograms of FIGS. 8 and 9 evidence that the primers comprising cytidine protected with Ac and subjected to the reagent (FIG. 8) and primers comprising cytidine protected with bz and subjected to ammonia (FIG. 9) were both extended at the 3' ends thereof, and that the resulting products were substantially identical.

The foregoing data evidences that the disclosed cleavage/deprotection reagent rapidly and effectively removes oligonucleotides from a solid support and removes the protecting groups therefrom. Additionally, the solubilized, deprotected oligonucleotides subjected to such reagent are, inter alia, biologically useful. Furthermore, the disclosed reagent comprising a TSA substantially reduces side product formation.

By varying the times and temperatures at which oligonucleotides are subjected to the reagent, the disclosed reagent can be utilized in a variety of contexts vis-a-vis synthesis of oligonucleotides. E.g., increase throughput on automated synthesizers; cleavage and deprotection of insolubilized and protected oligonucleotides; cleavage of insolubilized, protected oligonucleotides (i.e. where it is desirable to maintain protected oligonucleotides in solution); deprotection of soluble oligonucleotides (i.e. where the investigator has stored soluble, protected oligonucleotides; and deprotection of insoluble oligonucleotides (i.e., where the investigator has stored protected, insoluble oligonucleotides).

While the foregoing has been described in considerable detail, it is to be understood that the embodiments disclosed in the Detailed Description and Examples are not to be construed as limiting to the disclosure or the claims to follow. The invention is not limited to automated DNA synthesizers. The invention is not limited to deoxyribonucleic acid oligonucleotides, but can also be utilized with ribonucleic acid oligonucleotides and other modified oligonucleotides such as oligonucleotide methyl phosphonates and phosphorothioates. The invention is not limited to the specified protecting groups for any of the nucleosides, but can be utilized with a variety of protecting groups. Modifications and changes that are within the purview of those skilled in the art are intended to fall within the scope of the following claims.

---

What is claimed is:

1. A reagent for cleaving a support bound oligonucleotide and/or removing at least one protecting group from a protected oligonucleotide, the reagent comprising a volume ratio of about 1:1 aqueous methylamine:aqueous ammonia said aqueous methylamine consisting essentially of 40 wt % methylamine amine in water and said aqueous ammonia consisting essentially of about 29 wt % ammonia in water.

2. A reagent for cleaving a support bound oligonucleotide and/or removing at least one protecting group from a protected oligonucleotide, the reagent comprising a volume ratio of from about 3:7 aqueous methylamine:aqueous ammonia to about 7:3 aqueous methylamine:aqueous ammonia said aqueous methylamine consisting essentially of 40 wt % methylamine amine in water and said aqueous ammonia consisting essentially of about 29 wt % ammonia in water.

* * * * *